United States Patent [19]

Levy

[11] Patent Number: 5,158,720
[45] Date of Patent: Oct. 27, 1992

[54] METHOD AND SYSTEM FOR CONTINUOUS IN SITU MONITORING OF VISCOSITY

[75] Inventor: Ram L. Levy, Creve Coeur, Mo.

[73] Assignee: McDonnell Douglas Corporation, Creve Coeur, Mo.

[21] Appl. No.: 430,098

[22] Filed: Aug. 28, 1990

Related U.S. Application Data

[63] Continuation of Ser. No. 161,351, Feb. 22, 1988, abandoned, which is a continuation of Ser. No. 806,493, Dec. 9, 1985, abandoned.

[51] Int. Cl.$^5$ .................. B29C 35/02; G01N 21/64
[52] U.S. Cl. .................. 264/21; 250/227.14; 264/40.1; 264/40.2; 356/133; 436/55; 436/172
[58] Field of Search .................. 264/21, 40.1, 40.2; 436/55, 172; 250/227.14; 356/133

[56] References Cited

U.S. PATENT DOCUMENTS

| | | | |
|---|---|---|---|
| 3,659,974 | 5/1972 | Neugroachl | 425/29 |
| 3,791,792 | 2/1974 | Lindsay | 264/40.2 X |
| 3,935,053 | 1/1976 | Armstrong, Jr. | 264/40.2 X |
| 4,003,707 | 1/1977 | Lübbers, et al. | 436/68 X |
| 4,044,600 | 8/1977 | Claxton et al. | 73/15 R |
| 4,075,493 | 2/1978 | Wickersheim | 250/461 R |
| 4,215,275 | 7/1980 | Wickersheim | 250/459 |
| 4,312,228 | 1/1982 | Wohltjen | 73/597 |
| 4,346,599 | 8/1982 | McLaughlin et al. | 73/597 |
| 4,440,699 | 4/1984 | Smid et al. | 264/40.2 X |
| 4,455,268 | 6/1984 | Hinrichs et al. | 264/40.2 X |
| 4,510,103 | 4/1985 | Yamaguchi et al. | 264/40.2 |
| 4,904,080 | 2/1990 | Afromowitz | 356/133 |

OTHER PUBLICATIONS

Oster, et al., J. Am Chem. Soc., 78, 1581 (1956) "Fluorescence and Internal Rotation".
Sharafy et al. J. Am. Chem. Soc., 93, 4119 (1971) Viscosity Dependence of Fluorescense Quantum Yields.
Law, Chemical Physics Letters, 75, 545 (1980) Fluorescence Probes for Microenvironments.
Law, Photochemistry and Photobiology, 33, 799 (1981) Fluorescence Probes for Microenvironments.
Loutfy, Macromolecules, 14, 270 (1981) High Conversion Polymerization Fluorescense Probes.
Senturia, et al., J. Adhesion, 15, 69 (1982) In-Situ Measurement of the Properties of Curing Systems.
Förser, et al. Z. Phys. Chem, 75(1-2), 63 (1971) Effect of Viscosity on the Fluorescense Yield of a Dye.
Loutfy, J. Polymer Sci, 20,825 (1982) Fluorescence Probes for Polymerization Reactions.
Loutfy, et al., Macromolecules, 16, 452 (1983) Effect of Polymer Chain Tacticity on Fluorescence.
Levy, Am. Chem Soc. Apr. 1984 Viscosity Dependent Self-Probe Fluorescence of an Epoxy Resin.

Primary Examiner—Jill Johnston
Attorney, Agent, or Firm—Edward H. Renner

[57] ABSTRACT

An apparatus and method for in situ monitoring the viscosity and cure of resins using viscosity dependent fluorescence uses a fiber optic waveguide to introduce light to the resin of a wavelength exciting fluorescence and to conduct the emitted light to a monitor. The emitted light parameters correlate to the viscosity and cure conditions of the resin. The apparatus and method may be used to control composite construction and to provide information on the in service condition of composites.

13 Claims, 6 Drawing Sheets

METHOD AND SYSTEM FOR CONTINUOUS IN SITU MONITORING OF VISCOSITY

This is a continuation of copending application Ser. No. 07/161,351 filed on Feb. 22, 1988; now abandoned which is a continuation of copending application Ser. No. 806,493 filed on Dec. 9, 1985, now abandoned.

BACKGROUND AND SUMMARY OF THE INVENTION

This invention relates to a method and a system for monitoring viscosity and in particular to a fiber-optic system for continuous in situ monitoring of viscosity by monitoring viscosity-dependent fluorescence.

There are well known laboratory techniques for measuring viscosity, but these have limited application. There are many instances where it would be desirable to continuously monitor the viscosity of a substance in situ. For example it would be desirable to continuously monitor the viscosity in chemical processes to monitor the extent or the rate of chemical reactions. In a polymerization or resin cure process monitoring of viscosity would indicate the extent of reaction i.e. the degree of cure and thus permit greater control of the process and the resultant product. It would also be desirable to continuously monitor the viscosity of other substances such as lubricating oils, insulating oils, and hydraulic fluids to detect breakdown.

The present invention is a new method and system for the continuous in situ monitoring of the viscosity of a substance. The system monitors the viscosity of the substance by monitoring its fluorescence. Fluorescence is the emission of energy in the form of visible light in response to excitation or activation of the substance by radiation. Certain substances exhibit viscosity-dependent fluorescence, that is, the fluorescence of these substances is dependent upon the viscosity of the medium in which they are dissolved. Some of the substances that will be monitored exhibit viscosity-dependent fluorescence themselves; other substances can be doped with a viscosity-dependent fluorescent substance. Thus fluorescence can be used to measure viscosity and degree of cure.

It is generally accepted that in viscosity-dependent fluorescent substances the energy absorbed from external irradiation is emitted through fluorescence and through intramolecular torsional and twisting motions. In a low viscosity medium a substantial amount of the energy can be emitted through these intramolecular torsional and twisting motions resulting in low fluorescence yield. However, as the viscosity of the medium increases intramolecular torsional and twisting motions become progressively more inhibited, resulting in a gradual increase in fluorescence.

The level of fluorescence and thus the viscosity is measured by fiber-optic fluorometry. Fiber optic waveguides are used to transmit excitation energy, typically ultra violet light to the substance from a remote source. The same or different waveguides also transmit the resultant fluorescence from the substance to remote processing instruments. The fiber optic waveguides allow in situ monitoring at a location remote from the light source and processing instruments. Processing of the resultant fluorescent light includes isolating the wave lengths of interest with beam splitters and filters or with monochromators and measuring their intensities with photodiodes or photodiode arrays. The analog signals from the photodiodes can then be amplified, digitalized, and interpreted. Such interpretation may include comparison with a predetermined calibration table of corresponding viscosities, which can conveniently be done with a microprocessor.

The inventor's new method and system permits the continuous, in situ monitoring of the viscosity of a substance. The method and system achieve accurate monitoring at a relatively modest cost. The use of fiber optic waveguides allows in situ monitoring at locations remote from the monitoring equipment, such as inside reaction vessels or large autoclaves. The viscosity of the substance can thus be continuously monitored during a reaction or while in service. The fiber optic waveguide does not even have to be in physical contact, just optical contact, with the substance.

The inventor's method and system is particularly useful for the monitoring and control of the manufacture of composite materials. The properties of composite materials, for example carbon-epoxy composites, depend upon the chemical and rheological events occurring during the resin cure cycle. Thus the properties of a composite material can be controlled by controlling the cure cycle of the composite material. The ability to control the cure cycle depends upon the ability to monitor the polymerization process of the composite material as the resin cures. Thus an improvement in monitoring improves the control of the cure cycle and allows the process to approach the optimum conditions to maximize the desired properties of the composite and allows a greater degree of control over the end product. The ability to conduct continuous in situ monitoring of resin cure states, cure kinetics, and resin viscosity greatly enhances control over the mechanical properties of composite materials.

Rheological, thermoanalytical, and spectroscopic techniques that measure cure variables have been used in laboratory studies of resin cure behavior. Physical restrictions, however, prevent the application of these techniques to in situ measurements during curing of composite materials in a factory setting. Dielectric spectroscopy techniques have been the only commercially acceptable method of monitoring cure viscosity. Senturia, et al. have recently described a microdielectrometric method for measuring cure viscosities. See "In-situ Measurement of the Properties of Curing Systems with Microdielectrometry," *Journal of Adhesion* 15, p. 69 (1982), incorporated herein by reference.

Fortuitously, some resins used in composite materials exhibit viscosity-dependent fluorescence. For example, tetraglycidyldiaminodiphenylmethane epoxy, which is the main constituent of the widely used CIBA-GEIGY MY720 (TM) resin, exhibits viscosity-dependent fluorescence. Other resins, for example those based on diglycidyl ether of bisphenol A do not exhibit viscosity-dependent fluorescence. However, small amounts (in the range of about 0.1–0.5%) of a viscosity-dependent fluorescent material can be added to these resins.

The inventor's method and system permits continuous in situ monitoring of resin viscosity or the degree of cure by monitoring the fluorescence of the resin. This continuous monitoring applied to the cure of the resin in a composite material allows greater control over the cure process and thus greater control over the properties of the resulting composite. The continuous monitoring allows the cure process to be conducted to maximize the properties of the composite. The system achieves accurate monitoring at a relatively modest cost. The use of fiber optic waveguides allows in situ monitoring at locations remote from the monitoring equipment. The waveguides can even be incorporated directly into molds or dies for the composite to monitor cure in the molds during commercial fabrication processes. It is also possible to incorporate the waveguides into the composite to monitor interior cure and to monitor in service properties of the composite.

The method and system provides an alternative to dielectric spectroscopy, previously the only available method for in situ measurement of resin viscosity during cure.

The system also offers several advantages over the prior microdielectrometric methods for in situ measurement of viscosity. First, the system more accurately measures the cure process. The cure-induced changes in the fluorescence of the viscosity-dependent fluorescent resin are directly related to the changes on the molecular level since they reflect incorporation of the resin into the polymer network and the increase of the rigidity of that network. Thus measurement of fluorescence represents the underlying processes better than the measurement of electrical properties, as previously done. In fact, fluorescence has been found to be a function of resin viscosity, according to this formula:

$$\Phi_F = C\eta^n$$

Where $\Phi_F$ is the fluorescence yield, C is a constant for the viscosity-dependent fluorescent substance and $\eta$ is viscosity. n is a constant for the particular resin and has been found to vary from $\frac{1}{3}$ to $\frac{2}{3}$ for different compounds.

A second advantage over the prior viscosity monitoring techniques is that greater sensitivity to changes in viscosity can be achieved over broader range of viscosities by using several viscosity-dependent fluorescent substances each having a fluorescence change in a different range of viscosities. This effect can be achieved by selecting viscosity-dependent fluorescent substances the molecules of which have rotating groups of different dimensions. The substances with the larger rotating groups would be sensitive to changes at low and intermediate viscosities during early stages of cure, and substances with smaller rotating groups would be sensitive to changes at high viscosities during later stages of cure.

A third advantage over the prior method of viscosity measurement is that the fiber optic waveguides can monitor the resin cure without physical contact with the composite part or without disturbing it.

DETAILED DESCRIPTION OF THE PREFERRED EMBODIMENT

The following description of the preferred embodiment refers to the monitoring of the viscosity of a resin or the degree of cure in a composite material during cure for illustration purposes only. The method and system of this invention can be employed for the continuous in situ monitoring of viscosity of other substances.

Figure 1:
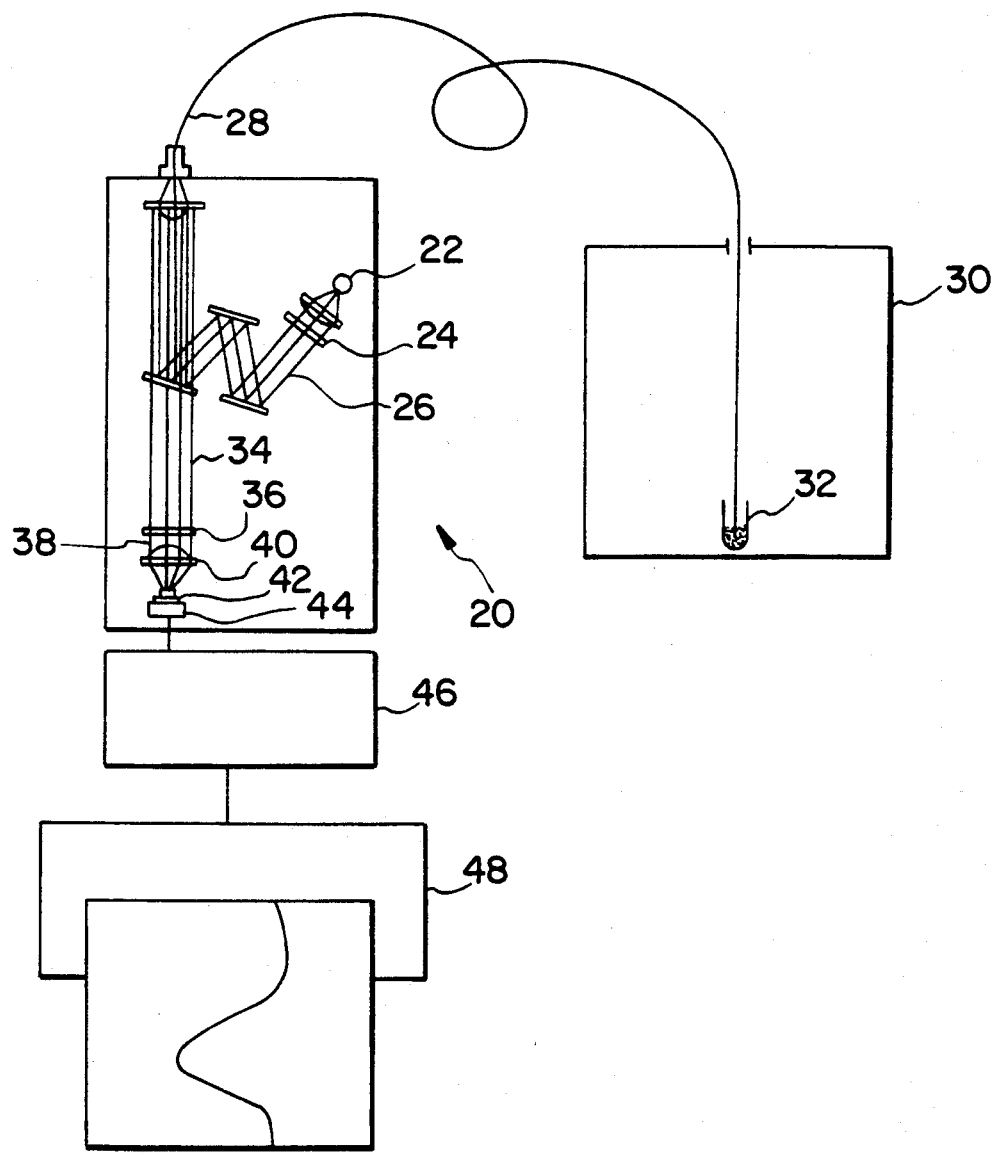
FIG. 1 is a schematic view of a system for monitoring resin viscosity employing the principles of this invention.

FIG. 1 is a schematic view of a system for the continuous in situ monitoring of resin viscosity, indicated generally as 20, incorporating the principles of this invention.

System 20 comprises a source of ultraviolet light 22. Ultraviolet light from source 22 passes through filter 24 which only transmits a beam 26 of the desired wavelengths (typically about 400-450 nm) of ultraviolet-visible light. Filtered light beam 26 is then directed to optic fiber waveguide 28. Optic fiber waveguide 28 extends from system 20 into a remote variable temperature oven 30 to a resin sample 32 curing in oven 30. Resin sample 32 could be, for example, tetraglycidyldiaminodiphenylmethane, which exhibits a viscosity-dependent fluorescence, cured with diaminodiphenyl sulfone. Resin sample 32 could also be, for example, diglycidyl ether of bisphenol A cured with diethylenetriamine, neither of which have viscosity-dependent fluorescence. In this case a viscosity-dependent fluorescent material must be added, such as about 0.1-0.5% polyester yellow dye of a series of p-(N,N-diaklyaminobenzylidene malonitriles possessing viscosity-dependent fluorescence.

Filtered visible-ultraviolet light beam 26 travels through optic fiber waveguide 28 and irradiates resin sample 32 in oven 30. The viscosity-dependent fluorescent material in resin sample 32 fluoresces under the excitation of beam 26. The resultant visible light 34 travels back through optic fiber waveguide 28 to system 20. Light 34 is passed through a filter 36 which only transmits a beam 38 of desired wavelengths of light. (Typically about 510 nm). Beam 38 is focused by a lens 40 onto a photodiode detector 42. The analog signal from detector 40 is boosted by preamplifier 44. The boosted signal is amplified by amplifier 46. The amplified signal is then transmitted to a recorder, such as chart recorder 48.

Figure 2:
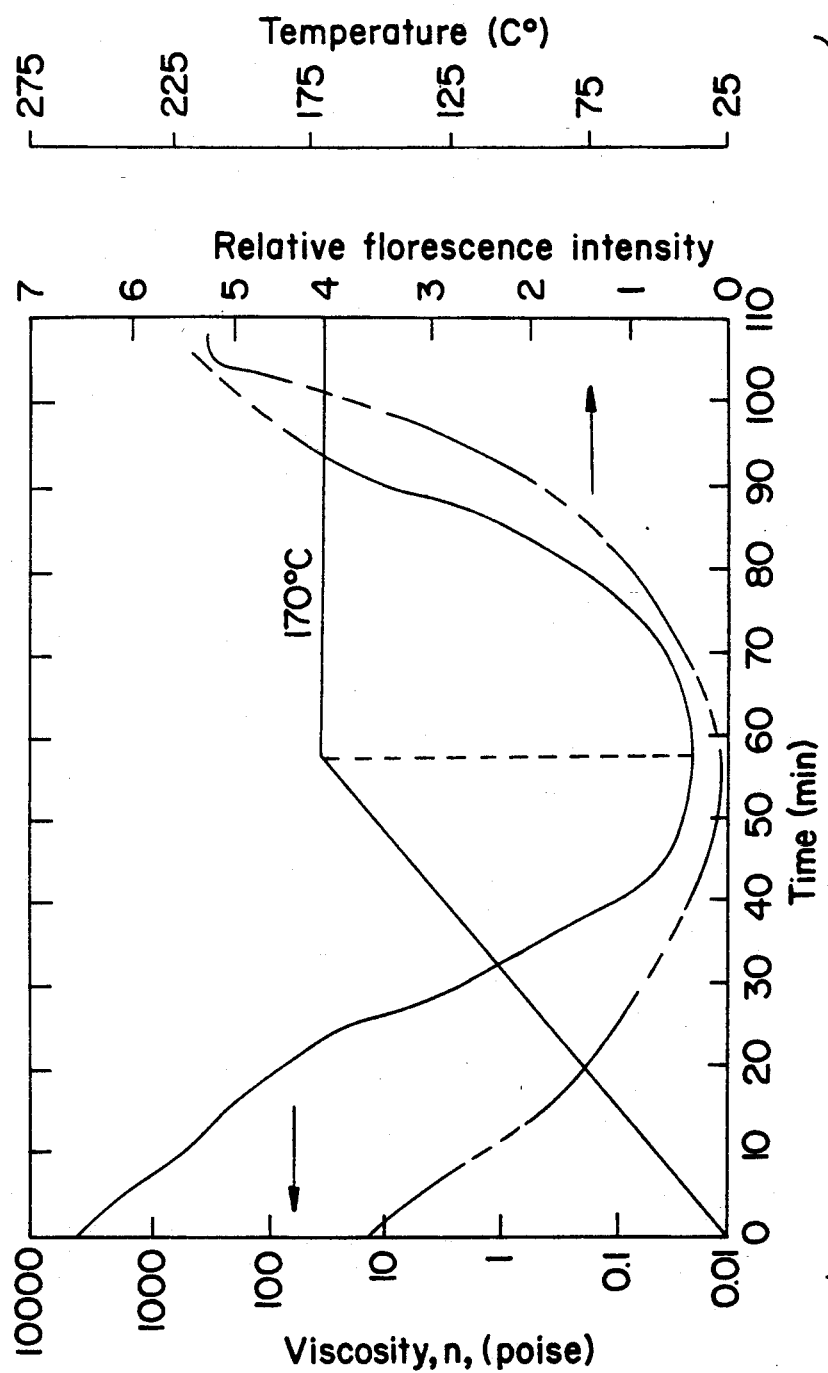
FIG. 2 is a typical graph of fluorescence versus time for a resin under cure derived according to the principles of this invention, compared with a graph of viscosity verses time for the resin under cure derived by rheometrics spectrometer.

FIG. 2 is a typical plot of fluorescence versus time for a resin under cure as would be determined with the system just described, compared to a graph of viscosity versus time for the resin under cure as determined by rheometrics spectrometer. The resin is tetraglycidyl-diaminodiphenylmethane cured with diaminodiphenyl sulfone. Fluorescence was monitored in the range of 505-525 nm. The viscosity was separately determined by dynamic rheometry. The results show that viscosity can be accurately determined by measuring fluorescence as the inventor has done.

Figure 3:
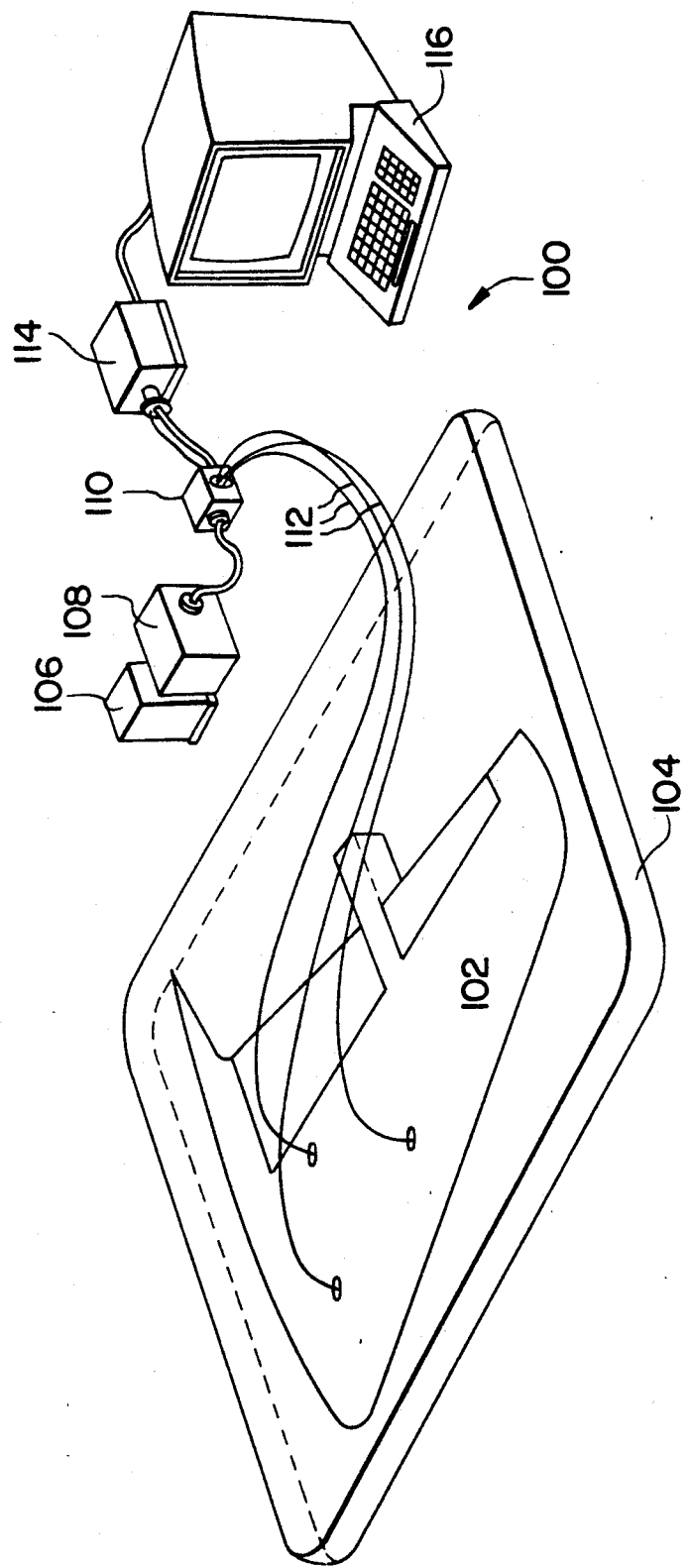
FIG. 3 is a view of the continuous in situ resin viscosity monitoring system set up to monitor a composite material while it is curing in an autoclave.

In FIG. 3, a system for continuous, in situ monitoring of resin viscosity, indicated generally as 100, is shown as it would be used to monitor a composite part 102 curing in an autoclave enclosure 104.

Part 102 can be made at least in part from a viscosity-dependent fluorescent material such as tetraglycidyldiaminodiphienylmethane cured with diaminodiphenyl sulfone. Alternatively, part 102 can be made from non-viscosity-dependent fluorescent materials, mixed with a small amount, e.g. 0.5%, viscosity-dependent fluorescent material, such as a polyester yellow dye of a series of p-(N,N-diakylamino) benzylidene malonitriles possessing viscosity-dependent fluorescence. Ideally, part 102 would be provided with several viscosity-dependent fluorescent substances, each having a pronounced fluorescence change in a different range of viscosities. This is achieved by selecting viscosity dependent fluorescent substances whose molecules have rotating groups of different dimensions. The substances with the larger rotating groups, such as dibutyl amino and dipropyl amino, are sensitive to chances at low and intermediate viscosities during early stages of cure, and substances with smaller rotating groups, such as dimethyl amino and diethyl amino, are sensitive to changes at high viscosities during later stages of cure.

System 100 comprises a light source 106, for example a high-intensity tungsten-halogen lamp. A monochromator 108 is optically connected to light source 106 and filters out undesirable wavelengths, allowing only selected wavelengths of light to pass. Generally wavelengths of about 400-450 nm are preferred. The filtered ultraviolet light passes through a beam splitter and filter unit 110 to optic fiber waveguides 112. Optic fiber waveguides 112 extend from unit 110 through remotely located autoclave enclosure 104 to part 102. Optic fiber waveguides 112 can be built into the mold or die for shaping part 102, which would make use of waveguides 112 easier, eliminating the need to separately apply the waveguides to each part made.

The filtered ultraviolet light travels through waveguides 112 to part 102 where it irradiates part 102. The viscosity-dependent fluorescent material fluoresceces under the stimulation of the ultraviolet light. The resultant visible light travels back through optic fiber waveguides 112 to beam splitter and filter unit 110. The returning light beam is split in unit 110 and each split beam is filtered to isolate a particular desired wave length or range of wave length. Each resulting filtered beam is focused as with a lens onto a photodiode detector 114. The signals from photodiode detector 114 are transmitted to a microprocessor 116, for processing. Such processing may include comparision of the signal representing fluorescence with a predetermined calibration table of corresponding viscosities to determine viscosity, or further translation into an indication of cure state. Microprocessor 116 can also be programmed to control the cure process, directing that cure variables, such as the temperature in autoclave 104, be varied in response to the input signal corresponding to viscosity, all according to a predetermined optimal cure cycle.

Figure 4:
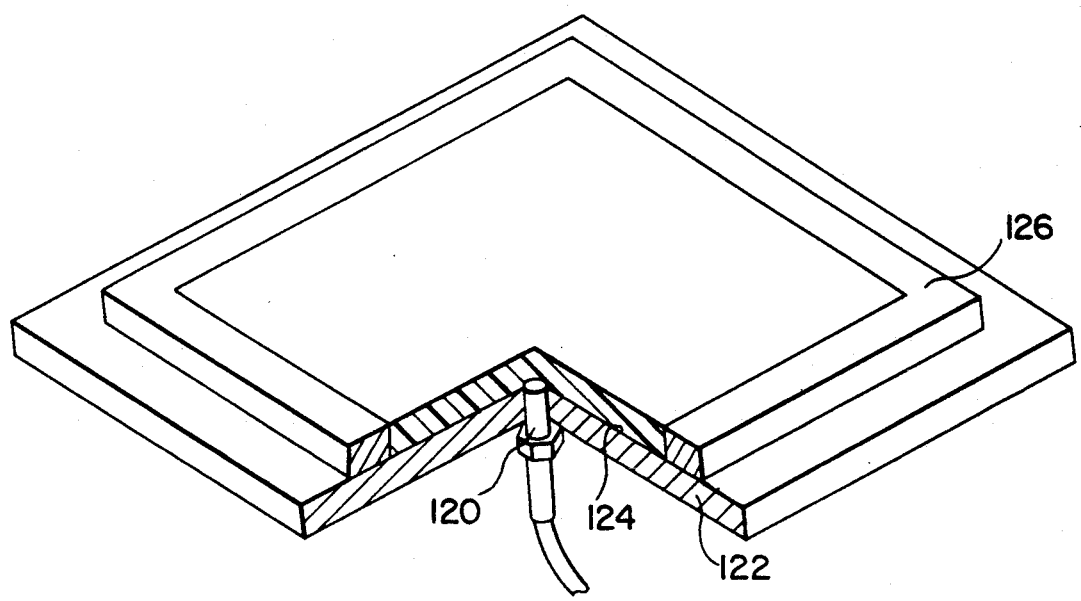
FIG. 4 is a perspective view of a fiber optic probe mounted in the surface of a tool to monitor a composite material while it is curing in an autoclave.

FIG. 4 illustrates the mounting of a fiber optic cure sensor 120 in a tool or mold 124 for the fabrication of composite parts, as would be done, for example, in system 100 just described. Tool 122 is typically made from aluminum, and has a surface 124 for shaping the part. Dams or sidewalls 126 surround tool 122 to contain the curing composite material 126. Sensor 120 extends through tool 122 and its distal or sensing end is mounted flush with surface 124. Permanently mounting probe 120 in tool 122 eliminates the need to install or set up the sensors for each manufacturing run. This reduces the time, labor, and cost required to use the system.

At high viscosities, particularly in the later stages of cure of epoxy composite, shifts in the wave length of the maximum intensity of emitted fluorescence $L_{max}^{em}$ and shifts in the wave length of the excitation radiation causing maximum intensity of emission $L_{max}^{em}$ have been observed. Adding wave length of the fluorescence maxima as a second parameter monitored allows the system to detect changes of viscosity at high viscosities where intensity changes are not as great. Monitoring $L_{max}^{em}$ during the cure of a composite allows the system to detect minor changes during the later stages of cure.

Figure 5:
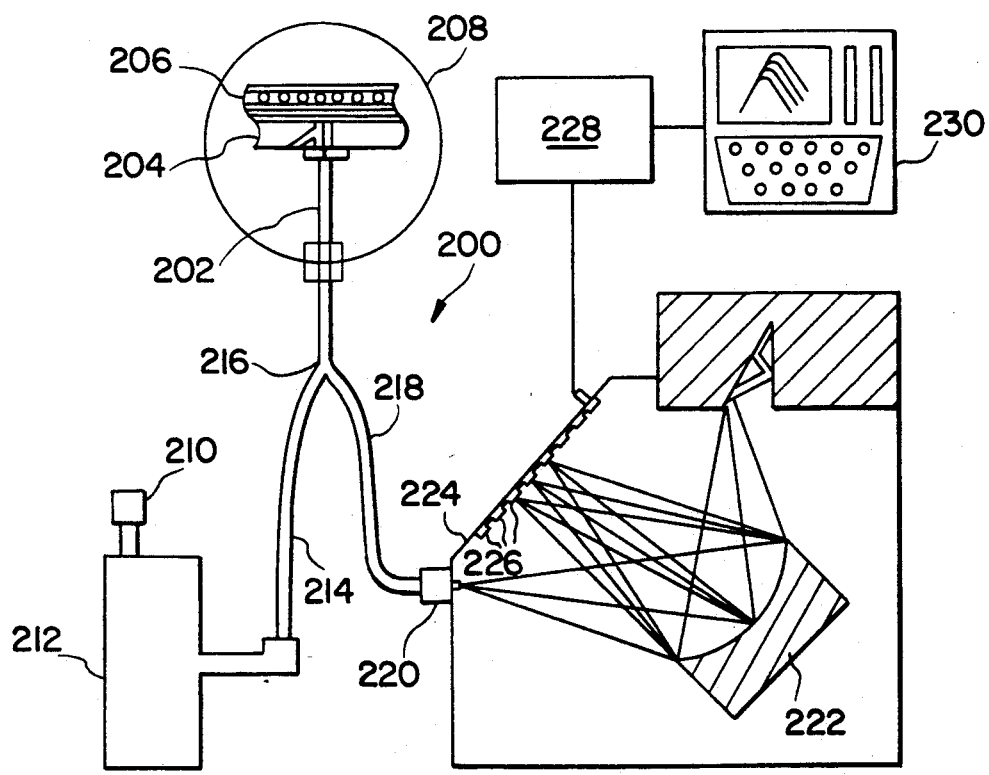
FIG. 5 is a schematic view of a system for monitoring resin viscosity capable of monitoring both intensity and wave length of fluorescence.

FIG. 5 is a schematic view of a system for the continuous in situ monitoring of resin viscosity, indicated generally as 200, capable of monitoring both the intensity and wave length of fluorescence. The system is shown as it would be connected to a tool-mounted fiber optic probe 202, mounted flush in the surface of a tool 204 as described above with regard to FIG. 4. A composite part 206 is curing in tool 204 which is positioned in an autoclave 208.

System 200 comprises light source 210 optically connected to a scanning monochromator 212. Scanning monochromator outputs excitation light to excitation optic fiber 214 in the ultra violet range, scanning a range of discrete wavelengths. This range is typically between about 395 and about 430 nm during early stages of cure (low viscosities) and between about 430 and 470 nm during later stages of cure (high viscosities). The excitation source scans at a rate of about 1 nm/sec. The excitation light is conducted by excitation fiber 214 through an optical Y tap 216 to waveguide 202. Waveguide 202 conducts the excitation light to composite material 206.

The excitation light causes composite material 206 to fluoresce. The emitted fluorescent light is conducted by waveguide 202, through Y tap 216, to detector fiber 218. The fluorescent light from detector fiber 218 is focused at 220 onto a diffraction grating 222 which splits up the light and focuses the light onto a photodiode array 224. Photodiode array 224 is comprised of a plurality of individual photodiodes 226 each of which measure the intensity of the particular wavelength or range of wavelengths focused on it. The output from photodiode array 224 is conducted to a diode array controller and digitizer 228, whose output is in turn conducted to microprocessor 230. Microprocessor 230 is programmed to identify the maximum intensity of the fluorescence and the $L_{max}^{em}$. The scanning of excitation wave lengths by scanning monochrometer 212 and the measurement of emitted fluorescence can be synchronized so that when the maximum intensity and $L_{max}^{em}$ for each excitation scan are identified, the $L_{max}^{em}$ for these values is known.

Microprocessor 230 can be programmed to compare the fluorescence intensity and $L_{max}^{em}$ with a predetermined calibration table of corresponding viscosities to determine viscosity, or further translate viscosity into some indication of cure state. Microprocessor 230 can also be programmed to control the cure process, directing that cure variables, such as the temperature in autoclave 208, be varied in response to the input signal corresponding to viscosity or degree of cure, all according to a predetermined optimal cure cycle.

Figure 6:
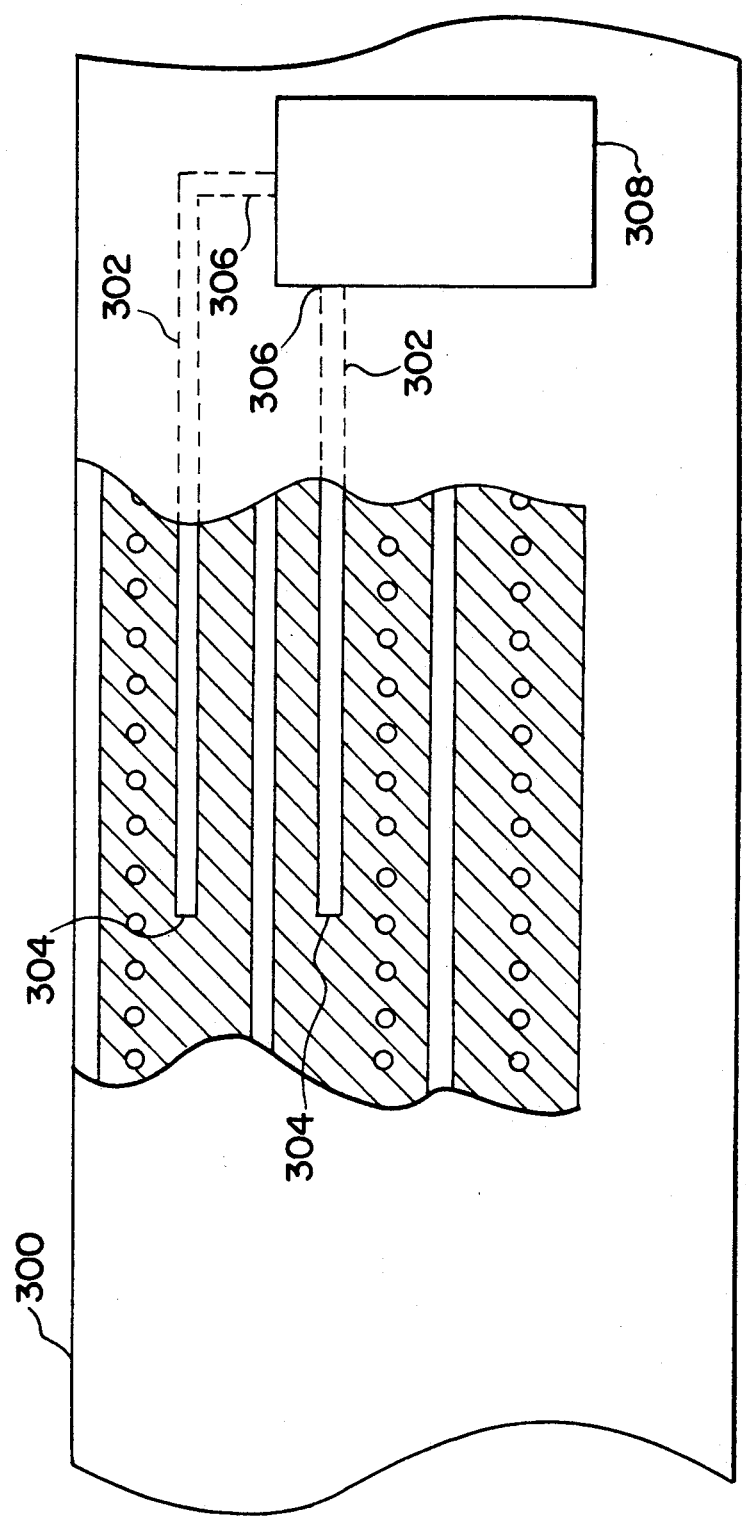
FIG. 6 shows a composite part fabricated with fiber optic waveguides for the continuous monitoring of resin while the part is in service.
Figure 7:
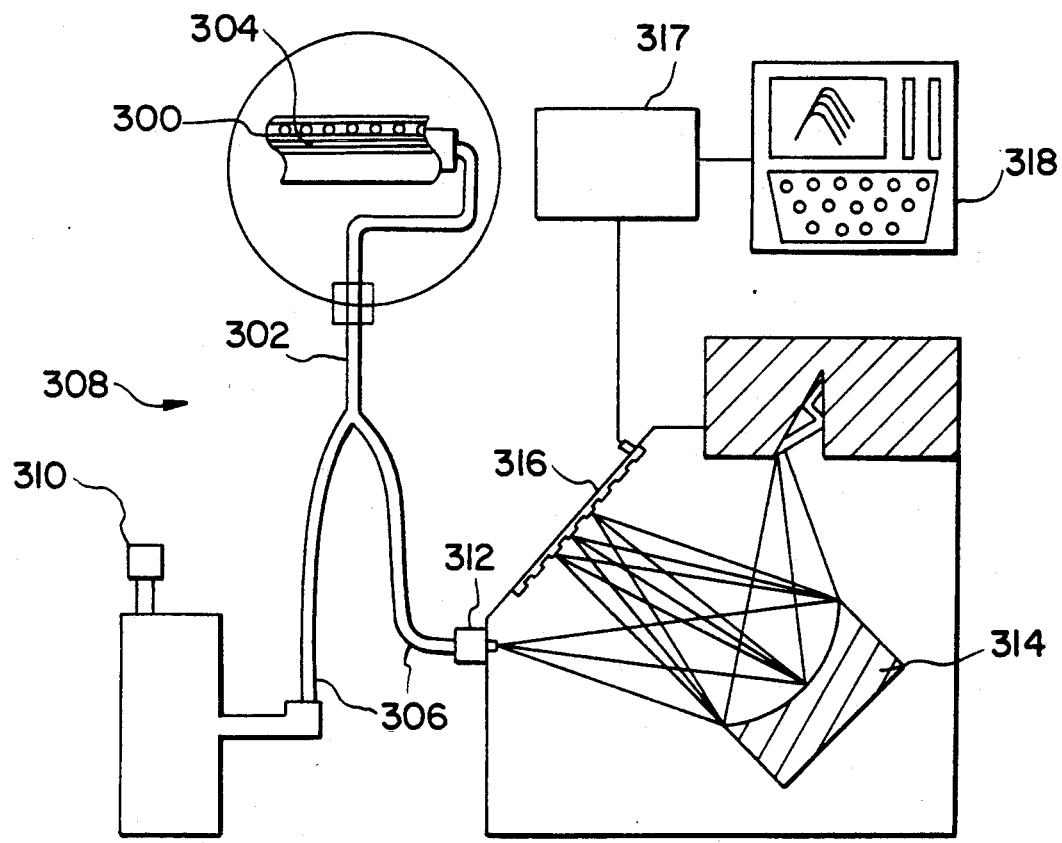
FIG. 7 is a schematic view of a system for monitoring the part shown in FIG. 6.

In FIG. 6 a plane wing 300 made from a carbon epoxy composite is shown as containing a plurality of fiber optic waveguides 302 extending therethrough. Waveguides 302 may be laid up with the wing and remain in place with the wing structure. The remote ends 304 of waveguides 302 are located at particularly sensitive or critical areas of wing 300. The inward ends 306 of waveguides 302 are connected to monitoring system 308. Monitoring system 308, shown schematically in FIG. 7, comprises a source of ultraviolet light 310 optically connected to the inward ends 306 of waveguides 302. Ultraviolet light from source 310 is conducted by waveguides 302 to the remote ends 304 where it irradiates the composite material at the sensitive or critical areas of the wing. Under the excitation or stimulation of the ultraviolet light the composite material or the viscosity-dependant fluorescent material therein, fluoresces. This light is conducted back along waveguide 302 to inward end 306. The fluorescent light is passed through a filter 312 which only transmits the wave lengths of interest and is focused as with lens 314 onto a photodiode detector 316.

The resulting signal from detector 316 is analyzed and compared to a norm. This can conveniently be done with a microprocessor 318. Microprocessor 318 can be preprogrammed to evaluate changes in fluorescence of the composite. Decreases in fluorescence are caused, for example, by water absorption, thermo-oxidation of the composite, or increased temperature. Increases in fluorescence are caused, for example, by over curing and embrittlement of the composite. Microprocessor 318 can be preprogrammed to evaluate these changes during the use of wing 302 and give appropriate warning when the condition of wing 302, as determined by fluorescence, deteriorates to an unacceptable condition for anticipated in-service conditions.

There are various changes and modifications which may be made to applicant's invention as would be apparent to those skilled in the art. However, any of these changes or modifications are included in the teaching of applicant's disclosure and he intends that his invention be limited only by the scope of the claims appended hereto.

I claim:

1. An improved method of forming a composite material into a desired shape by shaping the composite material and curing it, the improvement comprising the steps of:
    monitoring the fluorescence of the composite with a fiber optic waveguide to measure viscosity;
    adjusting the cure conditions in response to the measured viscosity or degree of cure according to a predetermined cure cycle.

2. The improved method of claim 1 wherein the temperature of cure is adjusted in response to the measured viscosity according to a predetermined cure cycle.

3. The improved method of claim 1 wherein the steps of monitoring the fluorescence comprises:
    providing at least one viscosity dependent fluorescent substance in the composite material;
    conducting excitation energy to the composite material with a fiber optic waveguide;
    conducting emitted fluorescence from the composite material with the fiber optic waveguide;
    measuring the emitted fluorescence of the composite material;
    translating the measured value of emitted fluorescence into a measure of viscosity.

4. The method of claim 3 wherein in the translation of the measured value of fluorescence into a measure of viscosity is according to the relation $\Phi = c\eta^n$ where $\Phi_F$ is fluorescent yield, C is a constant for the viscosity-dependent fluorescent substance, $\eta$ is viscosity, and $\eta$ is a constant for the resin.

5. The method of claim 3 wherein the translation of the measured value of emitted fluorescence into a measure of viscosity comprises comparing the measured value of emitted fluorescence with a predetermined calibration table of corresponding viscosities.

6. The method of claim 3 wherein the emitted fluorescence is measured by measuring the intensity of the emitted fluorescent.

7. The method of claim 6 wherein the emitted fluorescence is measured by measuring the intensity of the emitted fluorescence in the range of the wavelength of the maximum emission intensity, $L_{max}^{em}$.

8. The method of claim 3 wherein the emitted fluorescent light is measured by measuring the wave length of the maximum emission intensity, $L_{max}^{em}$.

9. The method of claim 8 wherein the excitation energy is ultra violet light of wavelength in the range causing emission at the maximum intensity, $L_{max}^{em}$.

10. The method of claim 3 wherein the excitation energy is ultraviolet light.

11. The method of claim 3 wherein at least two viscosity-dependent fluorescent substances are provided in the composition, each of said substances having a relatively large fluorescence in a different range of viscosity.

12. The method of claim 3 wherein the emitted fluorescence is measured by measuring the wavelength of the maximum emission intensity, $L_{max}^{em}$.

13. The method of claim 12 wherein the excitation energy is scanned over a range of discrete wave lengths; the emitted fluorescence is measured to determine the wavelength of maximum emission intensity, and wherein the measured value being the wave length of maximum emission intensity, $L_{max}^{em}$.

* * * * *